United States Patent
Vuong et al.

(10) Patent No.: US 7,616,325 B2
(45) Date of Patent: *Nov. 10, 2009

(54) OPTICAL METROLOGY OPTIMIZATION FOR REPETITIVE STRUCTURES

(75) Inventors: Vi Vuong, Fremont, CA (US); Junwei Bao, Palo Alto, CA (US); Joerg Bischoff, Illmenau (DE)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/140,627

(22) Filed: Jun. 17, 2008

(65) Prior Publication Data

US 2008/0285054 A1 Nov. 20, 2008

Related U.S. Application Data

(63) Continuation of application No. 11/061,303, filed on Feb. 18, 2005, now Pat. No. 7,388,677.

(51) Int. Cl.
*G01B 3/22* (2006.01)
*G01B 11/24* (2006.01)
*G01B 11/30* (2006.01)
*G01B 13/16* (2006.01)
*G01B 15/04* (2006.01)
*G01B 17/06* (2006.01)
*G01B 21/20* (2006.01)

(52) U.S. Cl. .................. 356/601; 356/604; 702/167
(58) Field of Classification Search .......... 356/600–640
See application file for complete search history.

(56) References Cited

U.S. PATENT DOCUMENTS

| | | | |
|---|---|---|---|
| 5,442,676 A | 8/1995 | Fewster et al. | |
| 5,530,732 A * | 6/1996 | Takemi | 378/73 |
| 5,748,509 A | 5/1998 | Fewster et al. | |
| 5,773,174 A | 6/1998 | Koizumi et al. | |
| 5,965,309 A | 10/1999 | Ausschnitt et al. | |
| 6,256,100 B1 * | 7/2001 | Banet et al. | 356/432 |
| 6,429,930 B1 | 8/2002 | Littau et al. | |
| 6,522,413 B2 * | 2/2003 | Opsal et al. | 356/601 |
| 6,639,674 B2 | 10/2003 | Sokolov et al. | |
| 6,772,084 B2 | 8/2004 | Bischoff et al. | |
| 6,785,638 B2 * | 8/2004 | Niu et al. | 702/189 |
| 6,823,043 B2 * | 11/2004 | Fewster et al. | 378/86 |
| 6,891,626 B2 | 5/2005 | Niu et al. | |
| 6,917,433 B2 * | 7/2005 | Levy et al. | 356/630 |

(Continued)

OTHER PUBLICATIONS

Chemali, C. E. et al. (Aug. 2004). "Run-to-Run Critical Dimension and Sidewall Angle Lithography Control Using the Prolith Simulator," *IEEE Transactions on Semiconductor Manufacturing* 17(3):388-401.

(Continued)

*Primary Examiner*—Gregory J Toatley, Jr.
*Assistant Examiner*—Jarreas C Underwood
(74) *Attorney, Agent, or Firm*—Manuel B. Madriaga

(57) ABSTRACT

An optical metrology model for a structure to be formed on a wafer is developed by characterizing a top-view profile and a cross-sectional view profile of the structure using profile parameters. The profile parameters of the top-view profile and the cross-sectional view profile are integrated together into the optical metrology model. The profile parameters of the optical metrology model are saved.

20 Claims, 14 Drawing Sheets

U.S. PATENT DOCUMENTS

| | | | |
|---|---|---|---|
| 6,943,900 B2 | 9/2005 | Niu et al. | |
| 7,046,375 B2 | 5/2006 | Bischoff et al. | |
| 7,065,423 B2 * | 6/2006 | Prager et al. | 700/108 |
| 7,092,110 B2 | 8/2006 | Balasubramanian et al. | |
| 7,126,700 B2 * | 10/2006 | Bao et al. | 356/625 |
| 7,216,045 B2 | 5/2007 | Doddi et al. | |
| 7,330,279 B2 | 2/2008 | Vuong et al. | |
| 7,355,728 B2 * | 4/2008 | Li et al. | 356/625 |
| 7,382,447 B2 | 6/2008 | Mieher et al. | |
| 7,388,677 B2 * | 6/2008 | Vuong et al. | 356/601 |
| 7,427,521 B2 | 9/2008 | Bischoff et al. | |
| 2003/0028358 A1 * | 2/2003 | Niu et al. | 703/2 |
| 2004/0267397 A1 | 12/2004 | Doddi et al. | |
| 2006/0187466 A1 | 8/2006 | Li et al. | |

OTHER PUBLICATIONS

Haykin, S. (1999). *Neural Networks*. 2nd edition, M. Horton ed., Prentice Hall: Upper Saddle River, New Jersey, 9 pages (Table of Contents).

International Search Report and Written Opinion mailed Jan. 24, 2007, for PCT Application No. PCT/US2006/04151 filed Feb. 6, 2006, 12 pages.

International Search Report and Written Opinion mailed Sep. 25, 2007, for PCT Application No. PCT/US06/34610 filed Sep. 5, 2006, 8 pages.

Li, L. (1996). "Formulation and comparison of two recursive matrix algorithms for modeling layered diffraction gratings," *Journal of the Optical Society of America A* 13:1024-1035.

\* cited by examiner

OPTICAL METROLOGY OPTIMIZATION FOR REPETITIVE STRUCTURES

CROSS REFERENCE TO RELATED APPLICATION

The present application is a Continuation of U.S. application Ser. No. 11/061,303, filed Feb. 18, 2005, issued as U.S. Pat. No. 7,388,677 on Jun. 17, 2008, which is incorporated herein by reference in its entirety for all purposes.

BACKGROUND

1. Field

The present application relates to optical metrology, and more particularly to optical metrology model optimization for repeating structures.

2. Related Art

Optical metrology involves directing an incident beam at a structure, measuring the resulting diffracted beam, and analyzing the diffracted beam to determine various characteristics, such as the profile of the structure. In semiconductor manufacturing, optical metrology is typically used for quality assurance. For example, after fabricating a periodic grating structure in proximity to a semiconductor chip on a semiconductor wafer, an optical metrology system is used to determine the profile of the periodic grating. By determining the profile of the periodic grating structure, the quality of the fabrication process utilized to form the periodic grating structure, and by extension the semiconductor chip proximate the periodic grating structure, can be evaluated.

In optical metrology, an optical metrology model is typically developed to measure a structure. The optical metrology model can be expressed using metrology model variables. In general, the greater the number of metrology model variables that are allowed to float in developing the optical metrology model, the greater the accuracy of the measurements obtained using the optical metrology model. However, increasing the number of metrology model variables allowed to float also increases the amount of time needed to develop the optical metrology model. Additionally, in some cases, allowing too many metrology model variables can produce erroneous measurements.

SUMMARY

The top-view profiles of repeating structures in a wafer are characterized and parameters to represent variations in the top-view profile of the repeating structures are selected. An optical metrology model is developed that includes the selected top-view profile parameters of the repeating structures. The optimized optical metrology model is used to generate simulated diffraction signals that are compared to measured diffraction signals.

DESCRIPTION OF DRAWING FIGURES

The present application can be best understood by reference to the following description taken in conjunction with the accompanying drawing figures, in which like parts may be referred to by like numerals:

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology

Figure 1:
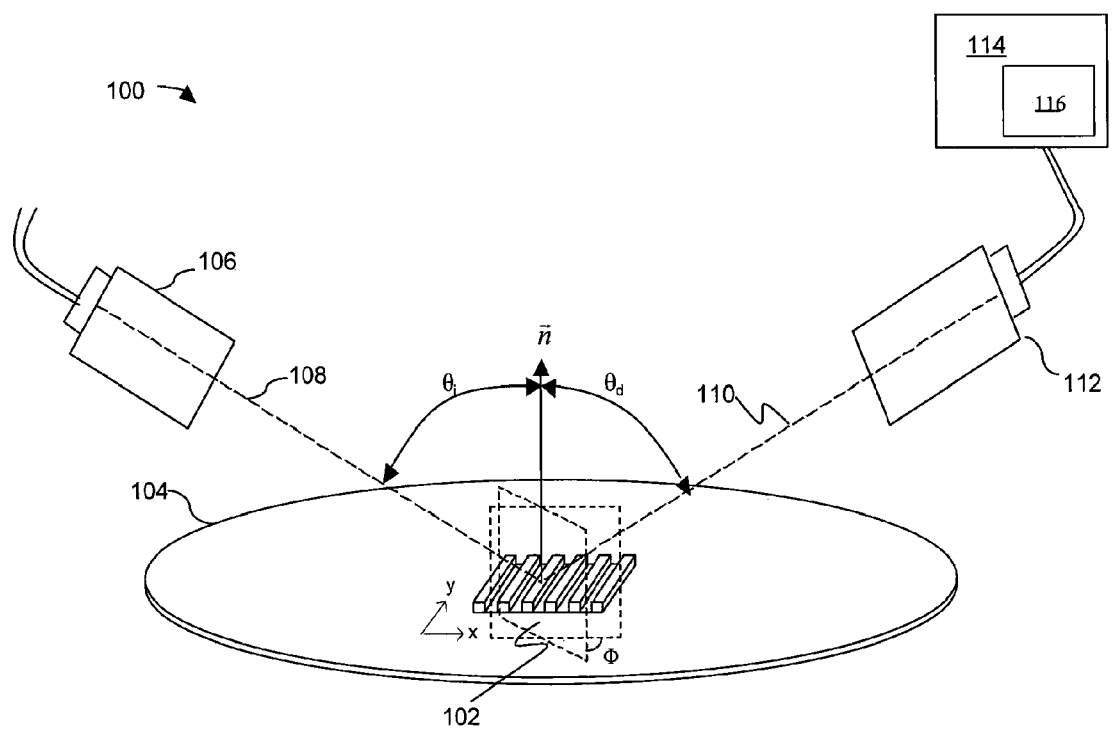
FIG. 1 is a block diagram of an exemplary optical metrology system.

With reference to FIG. 1, an optical metrology system 100 can be used to examine and analyze a structure. For example, optical metrology system 100 can be used to determine the profile of a periodic grating 102 formed on wafer 104. As described earlier, periodic grating 102 can be formed in test areas on wafer 104, such as adjacent to a device formed on wafer 104. Alternatively, periodic grating 102 can be formed in an area of the device that does not interfere with the operation of the device or along scribe lines on wafer 104.

As depicted in FIG. 1, optical metrology system 100 can include a photometric device with a source 106 and a detector 112. Periodic grating 102 is illuminated by an incident beam 108 from source 106. In the present exemplary embodiment, incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal $\vec{n}$ and is received by detector 112. Detector 112 converts the diffracted beam 110 into a measured diffraction signal.

To determine the profile of periodic grating 102, optical metrology system 100 includes a processing module 114 configured to receive the measured diffraction signal and analyze the measured diffraction signal. As described below, the profile of periodic grating 102 can then be determined using a library-based process or a regression-based process. Additionally, other linear or non-linear profile extraction techniques are contemplated.

2. Library-based Process of Determining Profile of Structure

In a library-based process of determining the profile of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing a hypothetical profile using a set of parameters, then varying the set of parameters to generate hypothetical profiles of varying shapes and dimensions. The process of characterizing a profile using a set of parameters can be referred to as parameterizing.

Figure 2A:
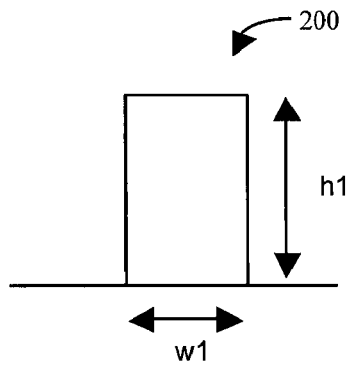
FIGS. 2A-2E are exemplary cross-sectional view profiles that characterize a structure formed on a semiconductor wafer.
Figure 2B:
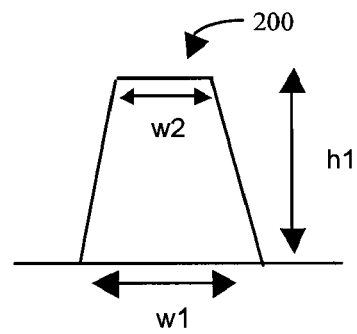
Figure 2C:
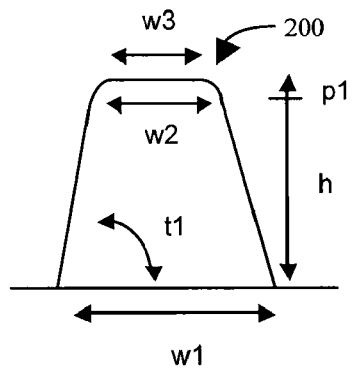
Figure 2D:
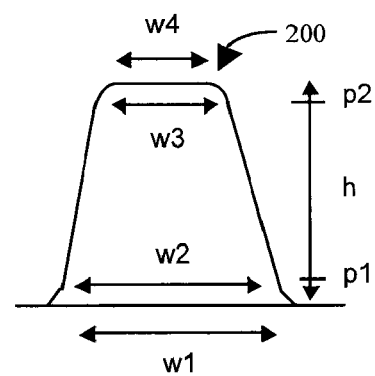
Figure 2E:
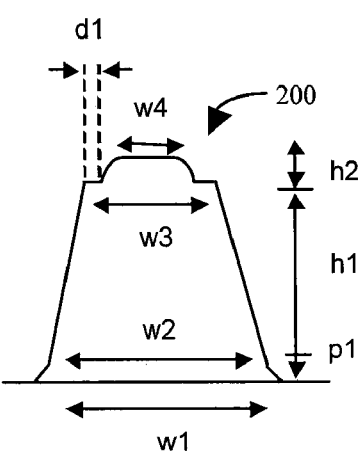

For example, as depicted in FIG. 2A, assume that hypothetical cross-sectional view profile 200 can be characterized by parameters h1 and w1 that define its height and width, respectively. As depicted in FIGS. 2B to 2E, additional shapes and features of hypothetical profile 200 can be characterized by increasing the number of parameters. For example, as depicted in FIG. 2B, hypothetical profile 200 can be characterized by parameters h1, w1, and w2 that define its height, bottom width, and top width, respectively. Note that the width of hypothetical profile 200 can be referred to as the critical dimension (CD). For example, in FIG. 2B, parameter w1 and w2 can be described as defining the bottom CD and top CD, respectively, of hypothetical profile 200.

As described above, the set of hypothetical profiles stored in library 116 (FIG. 1) can be generated by varying the parameters that characterize the hypothetical profile. For example, with reference to FIG. 2B, by varying parameters h1, w1, and w2, hypothetical profiles of varying shapes and dimensions can be generated. Note that one, two, or all three parameters can be varied relative to one another.

With reference again to FIG. 1, the number of hypothetical profiles and corresponding simulated diffraction signals in the set of hypothetical profiles and simulated diffraction signals stored in library 116 (i.e., the resolution and/or range of library 116) depends, in part, on the range over which the set of parameters and the increment at which the set of parameters are varied. In one exemplary embodiment, the hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using atomic force microscope (AFM), or a cross section scanning electron microscope (XSEM), a transmission electron microscope (TEM), and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-based Process of Determining Profile of Structure

In a regression-based process of determining the profile of a structure, the measured diffraction signal is compared to a simulated diffraction signal (i.e., a trial diffraction signal). The simulated diffraction signal is generated prior to the comparison using a set of parameters (i.e., trial parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is not within a preset or matching criterion, then processing module 114 can iteratively generate another simulated diffraction signal for another hypothetical profile. In one exemplary embodiment, the subsequently generated simulated diffraction signal can be generated using an optimization algorithm, such as global optimization techniques, which includes simulated annealing, and local optimization techniques, which includes steepest descent algorithm.

In one exemplary embodiment, the simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Algorithm for Determining Simulated Diffraction Signal

As described above, simulated diffraction signals are generated to be compared to measured diffraction signals. As will be described below, in one exemplary embodiment, simulated diffraction signals can be generated by applying Maxwell's equations and using a numerical analysis technique to solve Maxwell's equations. More particularly, in the exemplary embodiment described below, rigorous coupled-wave analysis (RCWA) is used. It should be noted, however, that various numerical analysis techniques, including variations of RCWA, modal analysis, integral method, Green's functions, Fresnel method, finite element and the like can be used.

In general, RCWA involves dividing a profile into a number of sections, slices, or slabs (hereafter simply referred to as sections). For each section of the profile, a system of coupled differential equations generated using a Fourier expansion of Maxwell's equations (i.e., the features of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. Specifically for a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

5. Machine Learning Systems

In one exemplary embodiment, simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

6. Repeating Structure

As described above, optical metrology has been traditionally performed on lines and spaces of periodic gratings with profiles that vary only in one dimension. In particular, with reference again to FIG. 1, the profile of periodic grating 102 varies in the x-direction but not in the y-direction. Thus, in performing optical metrology on such periodic gratings, only cross-sectional view profiles (such as those depicted in FIGS. 2A-2E) were used to characterize the profiles of the periodic gratings.

Figure 3A:
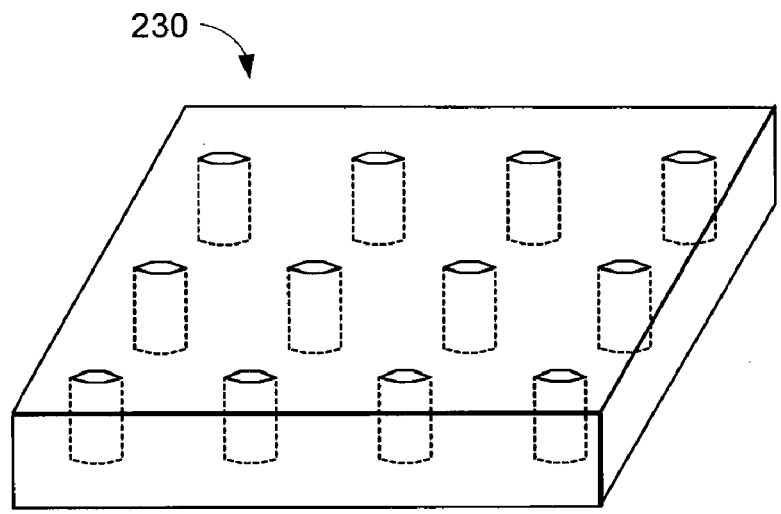
FIGS. 3A-3D depict exemplary repeating structures.
Figure 3B:
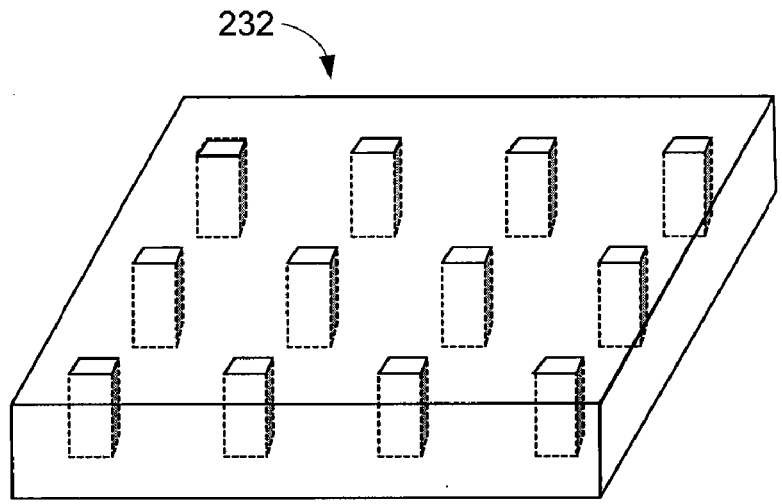
Figure 3C:
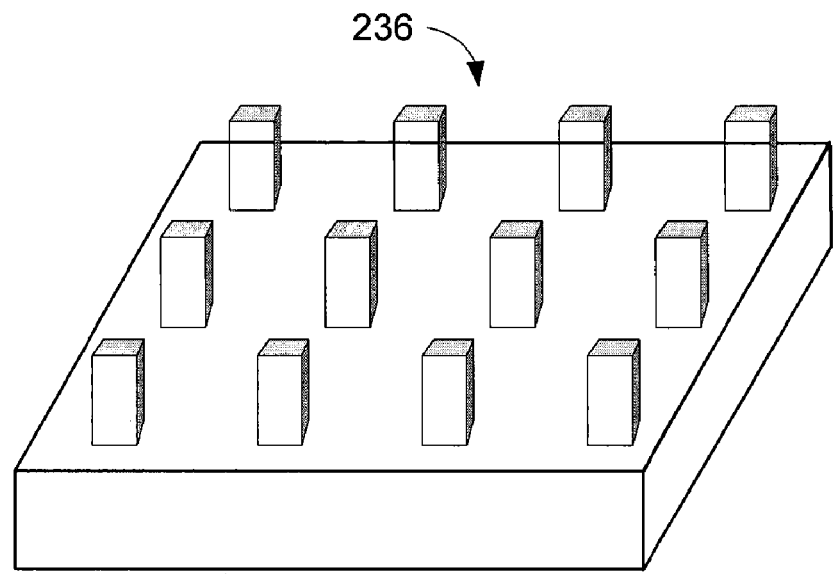
Figure 3D:
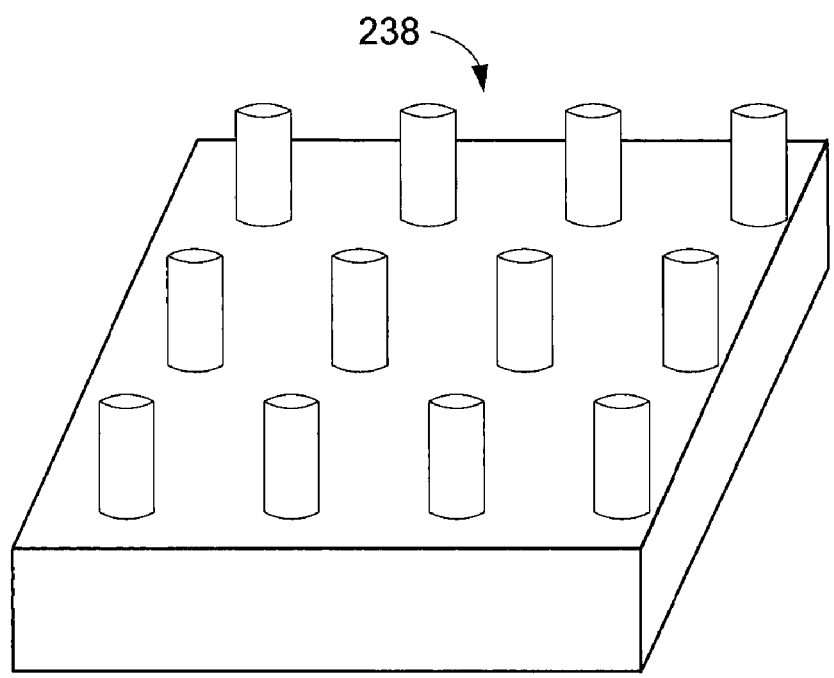

As depicted in FIGS. 3A-3D, various types of repeating structures can be formed on a wafer that have profiles that vary in at least two dimensions (e.g., in the x-direction and the y-direction in accordance with the coordinate system used in FIGS. 3A-3D). In particular, FIG. 3A depicts a repeating structure of substantially circular holes 230 formed through one or more layers of material. FIG. 3B depicts a repeating structure of substantially square holes 232 formed through one or more layers of material. FIG. 3C depicts a repeating structure of substantially square posts 236 formed above one of more layer of underlying material. FIG. 3D depicts a repeating structure of substantially circular posts 238 formed above one or more layers of underlying material. The square posts 236 of FIG. 3C and the circular posts 238 in FIG. 3D may be formed of one or more layers of material.

Figure 4A:
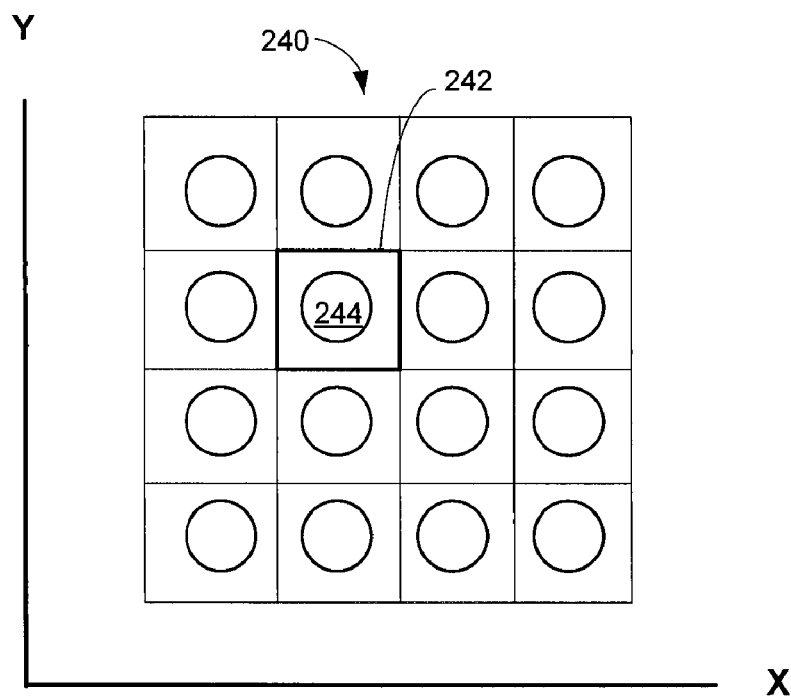
FIGS. 4A and 4B depict top views of exemplary orthogonal and non-orthogonal grids of unit cells.

FIG. 4A depicts a top-view of an exemplary repeating structure 240. A hypothetical grid of lines is superimposed on the top-view of the repeating structure 240 where the lines of the grid are drawn along the direction of periodicity. The profile of repeating structure 240 varies in two dimensions (i.e., the x-direction and the y-direction). The repeating structure 240 in FIG. 4A has two directions of periodicity (the x-direction and the y-direction). If the angle between the two directions of the periodicity is 90 degrees, the repeating structure is referred to as an orthogonal repeating structure; otherwise, it is referred to as a non-orthogonal repeating structure.

As depicted in FIG. 4A, the hypothetical grid of lines forms areas referred to as unit cells. In particular, FIG. 4A depicts an exemplary unit cell 242 with a feature 244, which is a hole, located substantially in the center of the unit cell 242. However, it is understood that the feature 244 may be located anywhere in the unit cell 242.

Figure 4B:
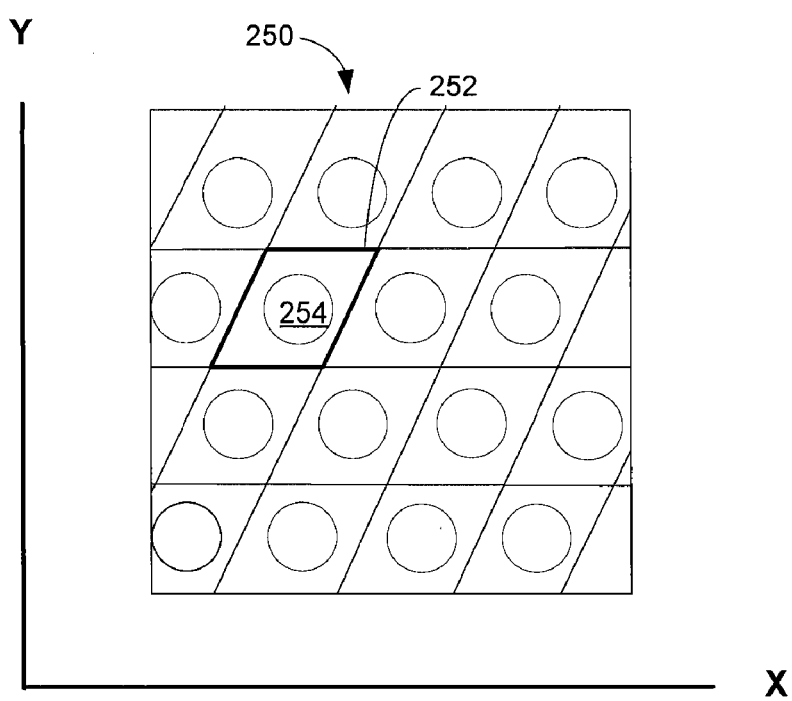

FIG. 4B depicts a top-view of an exemplary non-orthogonal repeating structure. In particular, FIG. 4B depicts an exemplary unit cell 252 that has a parallelogram shape and with a feature 254 located substantially in the center of the unit cell 252.

It should be recognized that a unit cell may have one or more features and the features may have different shapes. For example, a unit cell may have compound features such as a hole with an island inside the hole.

Figure 5:
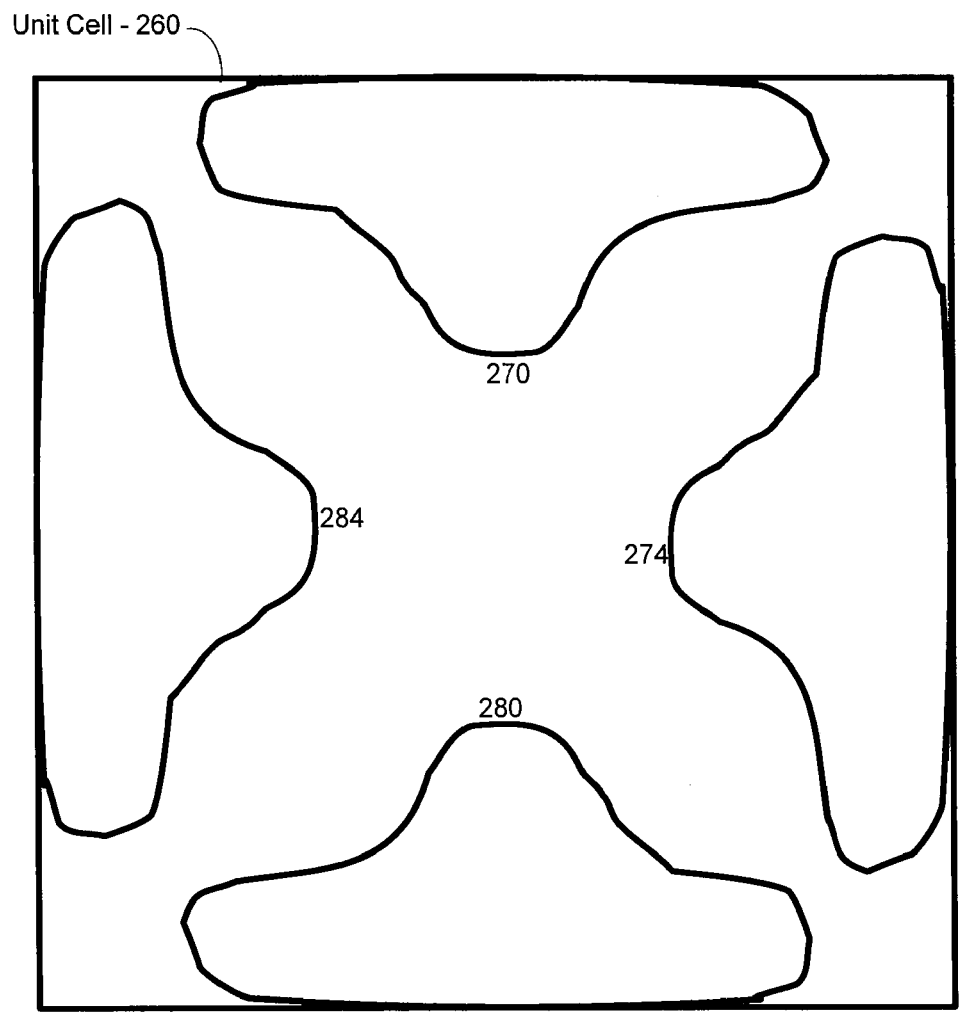
FIG. 5 depicts an exemplary unit cell comprising more than one feature in the repeating structure.

FIG. 5 depicts an exemplary unit cell with more than one feature. In particular, FIG. 5 depicts an exemplary unit cell 260 with four features. In FIG. 5, feature 270 is a pie-shaped structure with a bulge extending centrally below the main portion of the structure. Feature 280 is a pie-shaped structure with the bulge extending centrally above the main portion of structure. Feature 280 is a mirror image shape similar to feature 270. Feature 284 is a pie-shaped structure with the bulge extending to the right of the main portion. Feature 274 is also a pie-shaped structure with the bulge extending to the left of the main portion. Feature 274 is a mirror image shape similar to feature 284.

As mentioned above, it should be recognized that the features in a unit cell may be islands, posts, holes, vias, trenches, or combinations of the above. Furthermore, the features may have a variety of shapes and may be concave or convex features or a combination of concave and convex features.

Figure 6:
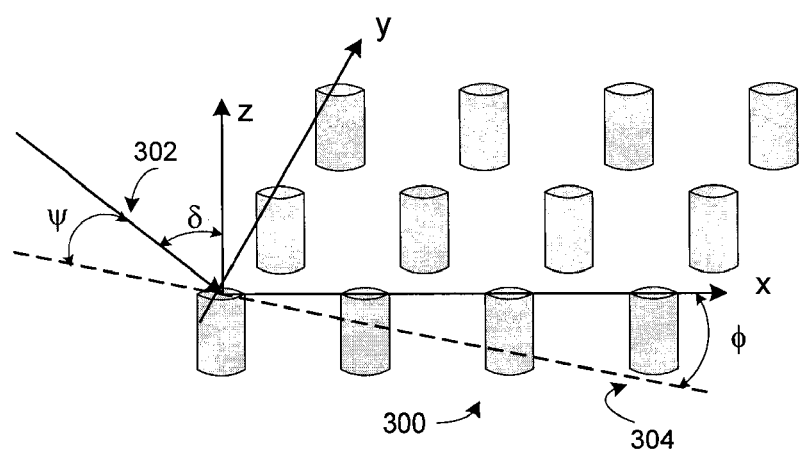
FIG. 6 depicts angles typically used to characterize exemplary repeating structures.

With reference to FIG. 6, in one exemplary embodiment, the profile of a repeating structure 300 is characterized using one or more profile parameters. In particular, the repeating structure 300, which can be a hole, post, or island, is characterized using a cross-sectional view profile, which represents the profile of the structure in the x-z plane, with the z-axis being normal to the wafer surface.

FIG. 6 depicts angles typically used as profile parameters in the cross-section view profile of the repeating structure 300. For example, $\delta$ is the polar angle of incidence of the incident beam 302 and the z axis. $\phi$ is the azimuthal angle of incidence of the incident beam 302 relative to the x axis (the angle between the projection of the incident beam into the x-y plane with the x-axis). $\psi$ is the polarization angle of the incident beam 302 relative to the horizontal line 304 representing the edge of a plane containing the incident beam 302. The underlying material in the repeating structure 300 in FIG. 6 is not shown in order to highlight the angles typically used to characterize repeating structures.

Figure 7A:
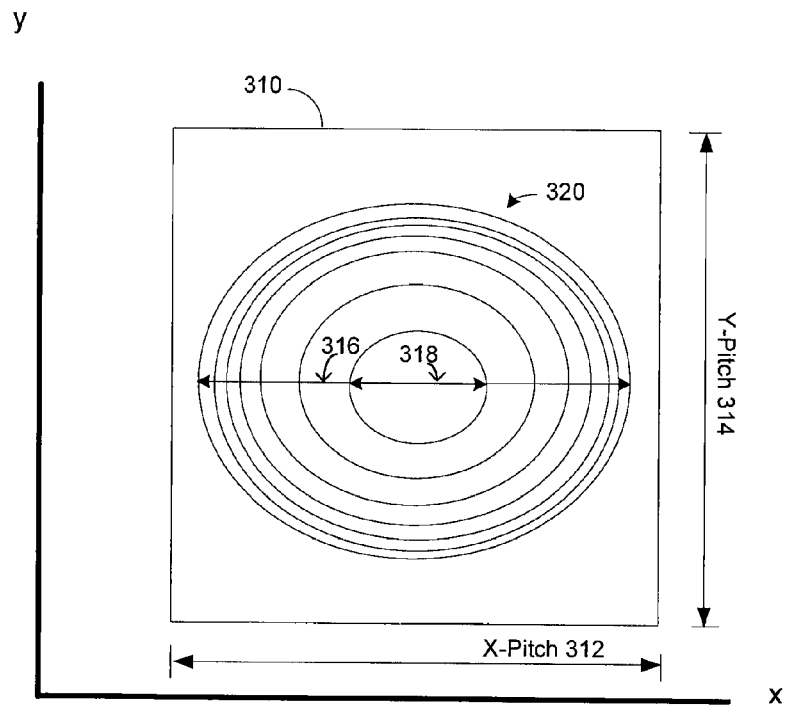
FIG. 7A depicts a top view profile of a repeating structure.

With reference to FIG. 7A, the top-view profile of a repeating structure is characterized using profile parameters. FIG.

7A depicts a top-view of a unit cell 310 with a feature 320, which is an elliptical hole with dimensions that become progressively smaller from the top of the hole to the bottom of the hole. Profile parameters used to characterize the top view profile includes the x-pitch 312 and the y-pitch 314. In addition, the major axis of the ellipse 316 that represents the top of the feature 320 and the major axis of the ellipse 318 that represents the bottom of the feature 320 may be used to characterize the feature 320. Furthermore, any intermediate major axis between the top and bottom of the feature may also be used as well as any minor axis of the top, intermediate, or bottom ellipse, (not shown).

Figure 7B:
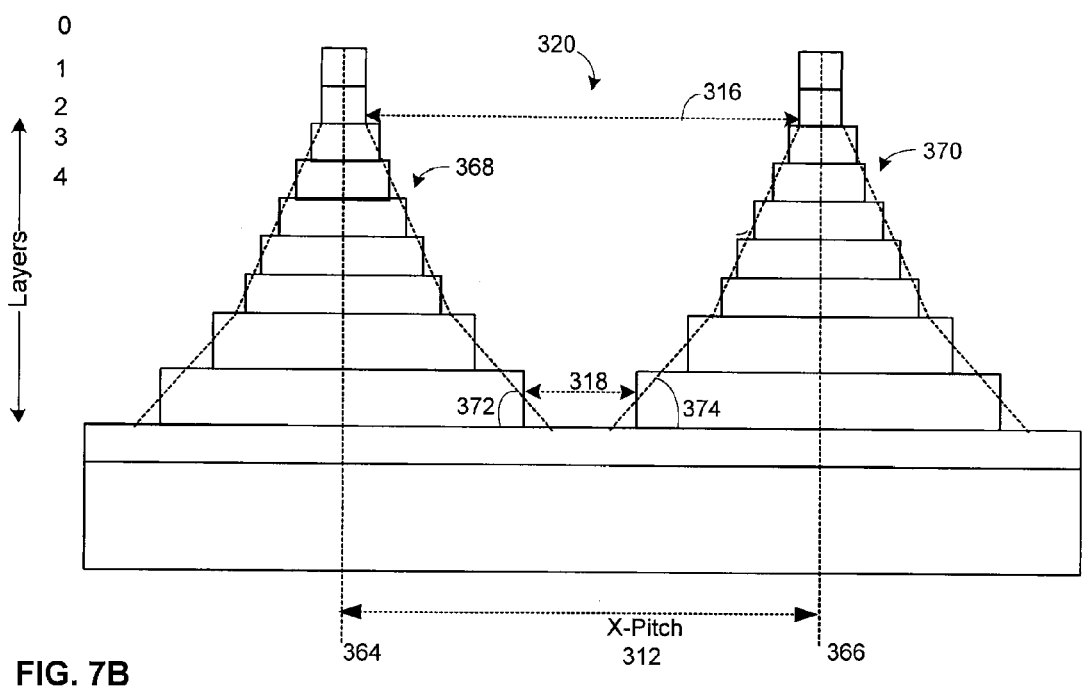
FIG. 7B depicts a cross-sectional view of the repeating structure.

With reference to FIG. 7B, the cross-sectional view profile of the repeating structure is characterized using profile parameters. As mentioned above, the cross-sectional view profile typically defined for analysis purposes represents the profile of the structure in the x-z plane, with the z-axis being normal to the wafer surface. Alternatively and/or additionally, the cross-sectional view profile can be defined in the y-z plane.

In the present example, the x-pitch 312 of the repeating structure is the distance between the centers of two of the adjacent sub-features 368 and 370. For illustration purposes, a dotted vertical line 364 is drawn through the center of sub-feature 368 and another dotted vertical line 366 is drawn through the center of sub-feature 370. The x-pitch 312 is the distance, typically in nanometers, nm, between the dotted vertical line 364 through sub-feature 368 and the dotted vertical line 366 through sub-feature 370.

Feature 320, including sub-features 368 and 370, are divided into layers, starting with layer 0, layer 1, layer 2, and so on. Assume layer 0 is air, layer 1 is material 1, layer 2 is material 3, etc. Layer 0 has an n and k of air, layer 1 has the n and k of material 1, etc. The distance 316 between the sub-features 368 and 370 is the same as the major axis 316 of the top of the feature 320 in FIG. 7A. Similarly, the distance 318 of sub-features 368 and 370 at the base of the feature 320 is the same as the major axis 318 of the bottom of the feature 320 in FIG. 7A. The slope of the feature 320 is characterized by angles 372 and 374. When the slop of feature 320 varies, angles 372 and 374 can vary along the z-axis. Alternatively, the slope of the feature 320 can be characterized using a mathematic formula, such as a polynomial function.

The profile parameters of the top-view profile and the cross-sectional view profile are integrated into an optical metrology model. In integrating the profile parameters, any redundant profile parameters are removed. For example, as described above, the profile parameters of the top-view profile includes x-pitch 312, y-pitch 314, major axis 316, and major axis 318. The profile parameters of the cross-sectional view profile includes x-pitch 312, major axis 316, major axis 318, n and k values for the layers, and slope of the feature. Thus, in this example, the profile parameters of the optical metrology model includes x-pitch 312, y-pitch 312, major axis 316, major axis 318, n and k values for the layers, and slope of the feature. See also, patent application Ser. No. 10/274,252, titled GENERATING SIMULATED DIFFRACTION SIGNALS FOR TWO-DIMENSIONAL STRUCTURES, filed on Oct. 17, 2002, which is incorporated herein by reference in its entirety.

Figure 8:
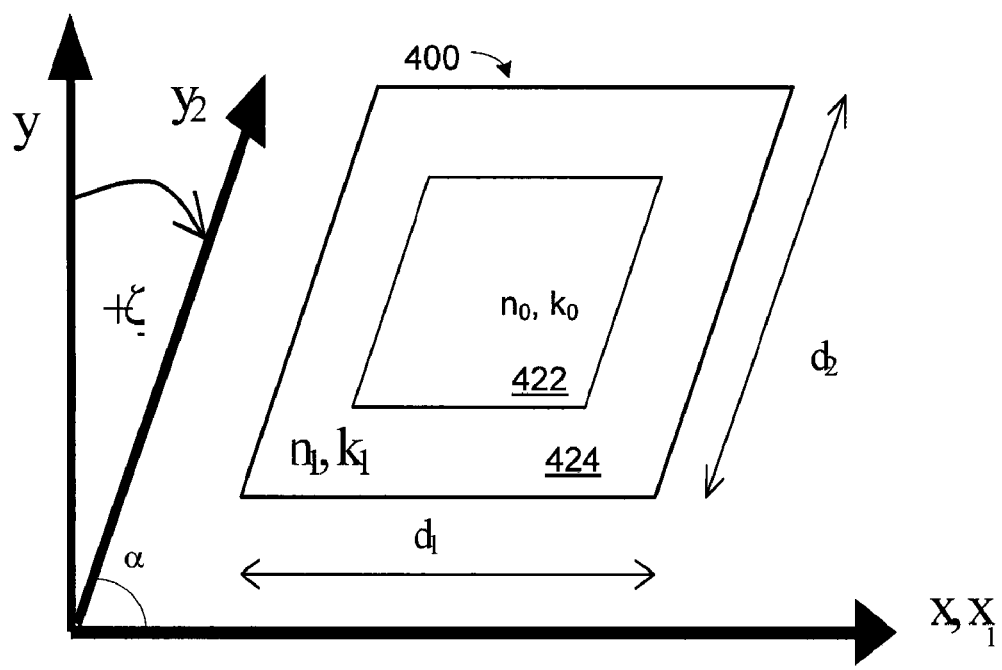
FIG. 8 depicts multiple features in a unit cell of an exemplary non-orthogonal repeating structure.

As mentioned above, unit cells in a repeating structure may be orthogonal and non-orthogonal. FIG. 8 depicts an exemplary non-orthogonal unit cell 400 of a repeating structure that includes a feature 422 that is a tetragonal hole. The feature 422 has refractive indices $n_0$ and $k_0$, that of air, and the rest of the material 424 in the unit cell 400 have refractive indices $n_0$ and $k_1$. The non-orthogonality is defined by the angle ζ, (Greek character zeta), which measures the deviation of the secondary axis $y_2$ in relation to the orthogonal y-axis. The angle ζ relates to the orthogonality or pitch angle α as equal to 90-ζ. Hereafter, the pitch angle will be used consistently to refer to the orthogonality or pitch angle α. The outer shape of the unit cell is described by the pitch in the secondary axis $x_1$ in the x direction and $y_2$ in the y direction, and pitch angle α, with the dimensions of the unit cell being $d_1$ and $d_2$. It is understood that the pitch angle may vary from −90 and +90 degrees.

Figure 9:
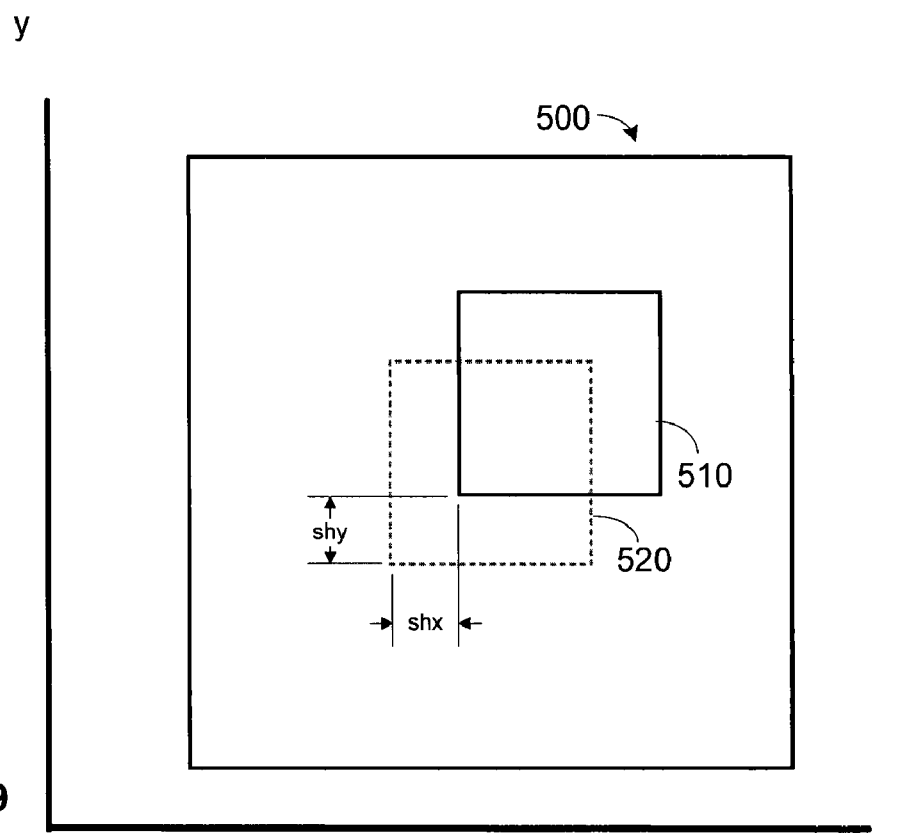
FIG. 9 depicts the offset of a feature in a unit cell from the theoretical center of an orthogonal unit cell of an exemplary repeating structure.

Other profile parameters associated with repeating structures is the position of the feature in the unit cell. FIG. 9 depicts the offset of a feature from the theoretical center of an orthogonal unit cell of an exemplary repeating structure. For example, in unit cell 500, a feature 510, instead of being positioned in the center of unit cell 500, may be situated a distance shy above and shx to the right of the center, designated by the dotted position 520.

Figure 10A:
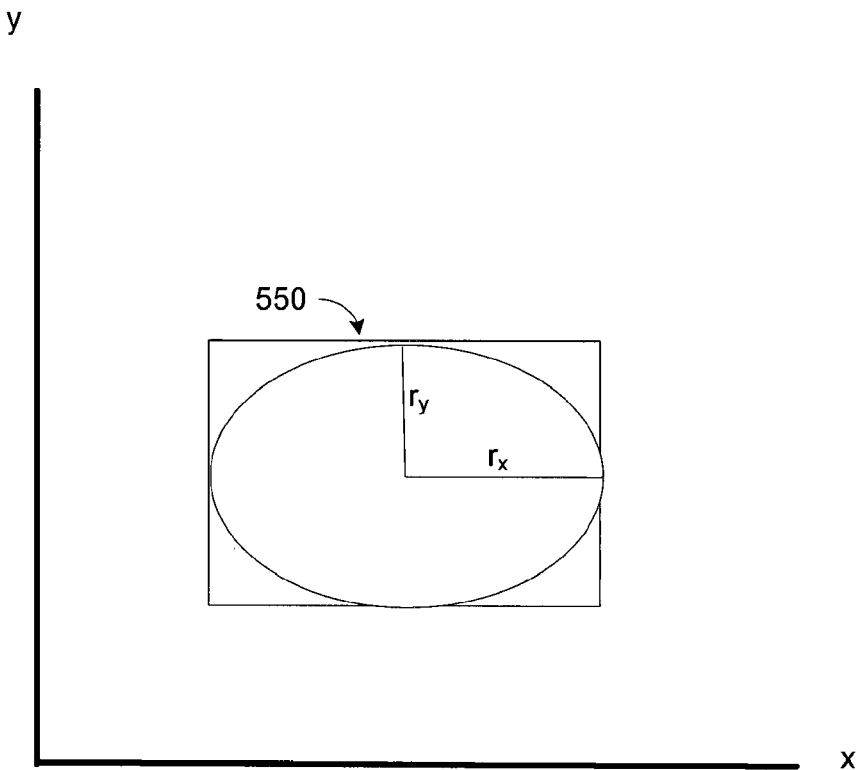
FIG. 10A depicts the width ratio of a feature in a unit cell.

In addition to the parameters for repeating structures discussed above, other parameters included in the characterization of the repeating structures are width ratio and rectangularity of the features in a unit cell. The width ratio parameter defines the amount of sharpness of the corners of the hole or island in the unit cell. As shown in FIG. 10A, in unit cell 550, the width ratio may be used to define the Y critical dimension of the shape relative to the X critical dimension. The width ratio $(WR)=r_y/r_x$ is a value that varies from less than 1 where the elliptical shaped-hole or island has a larger value for $r_x$ than $r_y$, a value of one for a circular hole or island or a value greater than 1 where the hole or island has a larger value for $r_y$ than $r_x$.

Figure 10B:
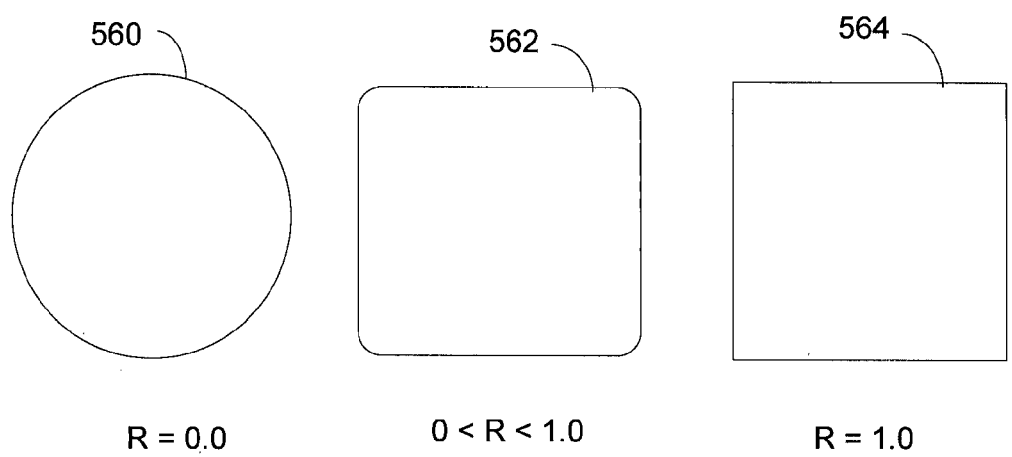
FIG. 10B depicts the rectangularity characterization of a feature in a unit cell.

Rectangularity defines the amount of sharpness of a feature such as a hole, post, or island in a unit cell. In FIG. 10B, a rectangularity R of 0.0 defines a perfectly circular hole or island 560, a rectangularity of greater than zero and less than 1.0 defines a rounded corner of a square-shaped hole or island 562, and a rectangularity of 1.0 defines square or rectangular-shaped hole, post, or island 564.

Another method of characterizing a feature of a unit cell is by utilizing a mathematical model of the feature. For example, the outer boundaries of a feature in a unit cell of a repeating structure such as a contact hole or a post can be described using one or more equations. In this modeling construct, a hole is a structure made of air, with a specific N and K much like an island is a structure with a different N and K. Therefore, a characterization of the boundaries of the features in a unit cell, such a hole, includes description of the shape and slope of the feature, as shown in cross-sectional view profile in FIG. 7B.

The top-view shape of the feature in the unit cell can be described mathematically by modifying the typical equation of an ellipse for a more general definition and by introducing exponents m and n:

$$x = a \cdot \cos^m(\phi+\phi_x) \text{ and } y = b \cdot \sin^n(\phi+\phi_y) \qquad 1.00$$

where x and y are the lateral coordinates of the shape in a section plane z that is constant, $\phi$ is the azimuthal angle, $\phi_x$ and $\phi_y$ are the azimuthal angle in the X and Y-axes, respectively, and $\phi=0 \ldots 2\pi$. If $m=2/M$ and $n=2/N$, M and N correspond to the exponents in the "standard" formula for a super-ellipse:

$$\left|\frac{x}{a}\right|^M + \left|\frac{y}{b}\right|^N = 1. \qquad 1.10$$

A more comprehensive parameter function is possible by using a universal representation that is achieved with a Fourier synthesis:

$$x(\varphi) = \sum_m a_m \cos^{Pm}(m \cdot \varphi + \varphi_{mx}) + x_0 y(\varphi) \quad 1.20$$
$$= \sum_n b_n \cos^{Pn}(n \cdot \varphi + \varphi_{ny}) + y_0$$

where $x_0$ and $y_0$ are the de-centering or lateral offset. Consecutive layers of the unit cell can be adjusted to each other by these de-centering parameters. In this way, complex repeating structures can be built by successively describing the layers of the structure.

The next step is to assign a slope (the third dimension) to the feature in the unit cell. This can be done using the parameter expression where the slope s is a function of t, or $\phi$, respectively. The complete description of the feature can be expressed with the following equations:

$$x = f(t); \, y = g(t); \text{ and } s = h(t) \quad 2.00$$

where f, g, and h are different functional characterization of the variable t and t may be the azimuthal angle $\phi$ or some other variable of the shape.

For instance, a feature shaped like an elliptical hole with ascending slopes on two opposite sides and re-entrant slopes on the two perpendicular sides may be given by:

$$x = a \cdot \cos \phi; \, y = b \cdot \sin \phi; \text{ and } s = 92° - c \cdot \arcsin(d \cdot |\sin \phi|) \quad 2.10$$

with $\phi = 0 \ldots 2\pi$, $c = 2°$, $d = 0.07$, the slope is 92° (i.e., slightly overhanging) along the x-axis, and about 88° (i.e., almost normal) along the y-axis, and the slope will change gradually between these extreme values. In this way, only linear slopes, both ascending and re-entrant can be covered. Non-linear slope forms can be addressed by assembling the feature with more than two non-uniform and non-scaling shapes. In order to describe non-linear shapes, an additional parameter z is introduced, resulting in the following equations:

$$x = f(t,z); \, y = g(t,z); \text{ and } s = h(t,z). \quad 2.20$$

where z is an expression that characterizes the non-linearity of the shapes.

Composite repeating structures where the unit cells that are formed by more than one material and where the features include more that one shape, are deconstructed into its building blocks and then treated as described above. It is understood that other mathematical representation of shapes in addition to those described above may be used to characterize the profile of features in a unit cell of repeating structure.

Figure 11:
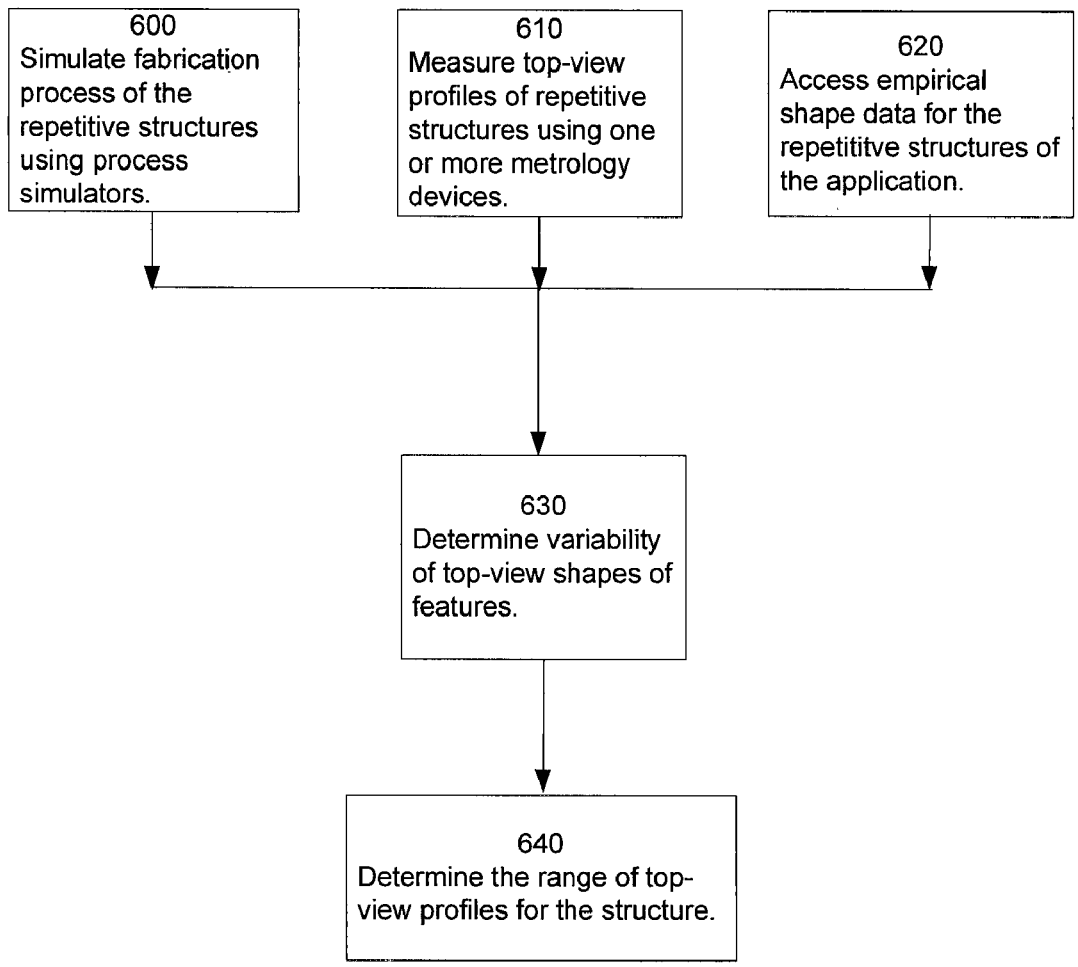
FIG. 11 is a flow chart of an exemplary process of collecting profile shape variability data for repeating structures.

In one exemplary embodiment, profile data is also used to characterize features in a unit cell. FIG. 11 is a block diagram of an exemplary method for collecting and processing of profile data of the repeating structure. In step 600 of FIG. 11, the fabrication process to produce the repeating structure may be simulated using process simulators. Examples of process simulators are Prolith™, Raphael™, and the like. One output of process simulators includes profiles of the resulting structure after the fabrication process is simulated. The profiles include profiles that can be analyzed for the type and variability of shapes produced based on variations of the process parameters. For example, if an etch process is simulated, the top-view profile of the resulting hole, post, or island can be examined to determine variability of the shapes after the process is completed under varying process conditions.

An alternative embodiment involves the measurement of profiles of repeating structures using one or more metrology devices, as in step 610, FIG. 11. Cross-section SEM, CDSEM, AFM, imaging systems, and like metrology devices may be used to measure the cross-sectional or top-view profiles of the repeating structures in a wafer. Similarly, optical metrology systems such as scatterometry devices, i.e., reflectometers and/or ellipsometers, may be used to determine the profiles of the repeating structures. Still another alternative embodiment include accessing empirical or historical shape data for the repeating structures of the application, as in step 620. The specific recipe or a similar semiconductor fabrication recipe may provide historical data related to the shape of the profiles of the subject structures.

In step 630 of FIG. 11, top-view profiles of the features in a unit cell obtained from various sources are examined to determine the variability of the feature shapes and profile parameters. In step 640 of FIG. 11, the range of the feature shapes of the structures may show a pattern where some aspect of the profile remain constant or vary only by a limited amount whereas other aspect of the profile exhibit a wide range of variability.

Figure 12:
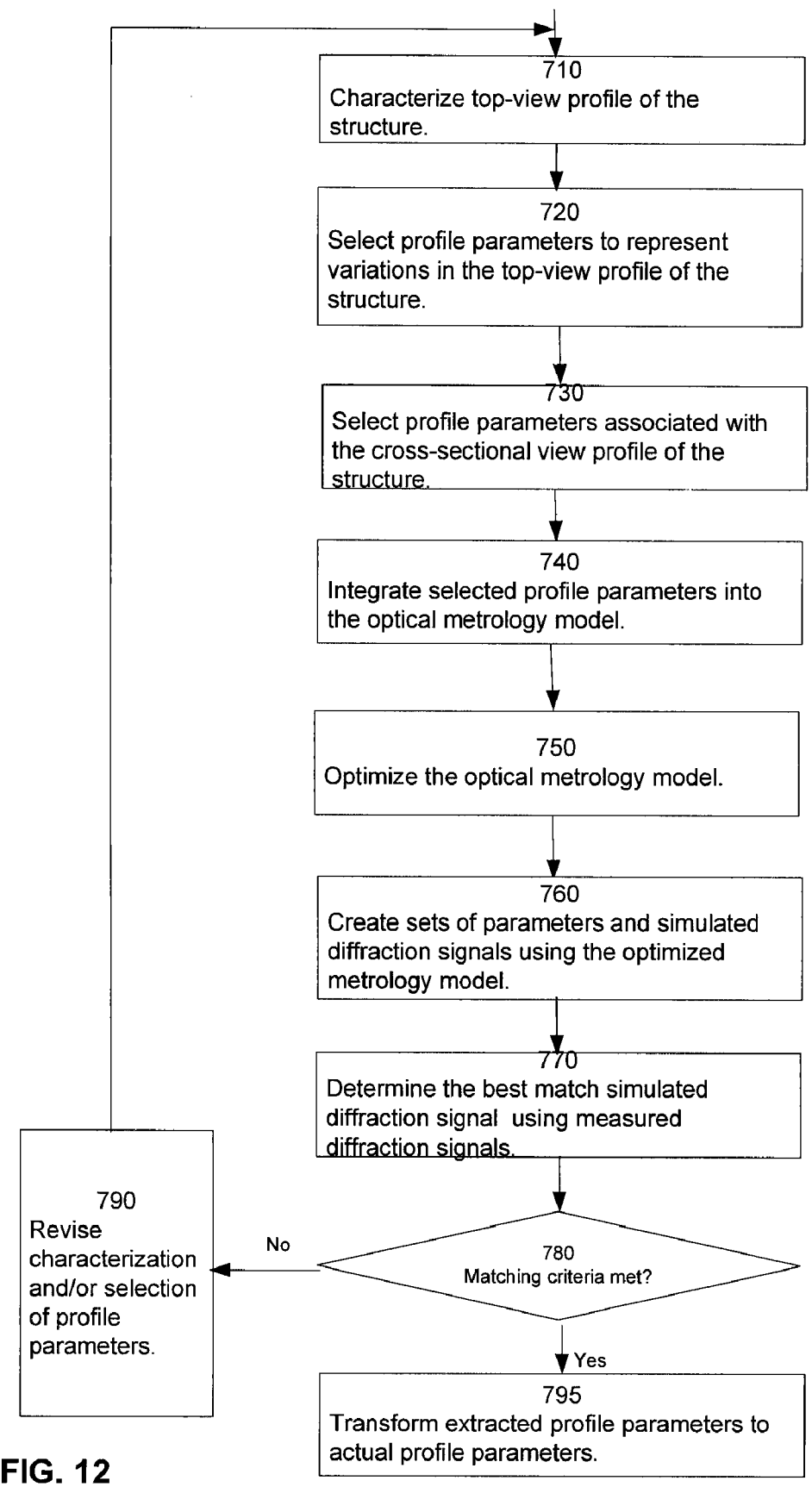
FIG. 12 is a flow chart of an exemplary process of optimizing an optical metrology model of a repeating structure.

FIG. 12 is a block diagram of an exemplary method for optimizing an optical metrology model of a repeating structure. Based on the data collected from various sources as discussed in the exemplary method depicted in FIG. 11, in step 710, the top-view profile of the structure is characterized either by fitting one or more geometric shapes, i.e., successive shape approximation or by utilizing the mathematical approach.

Figure 13:
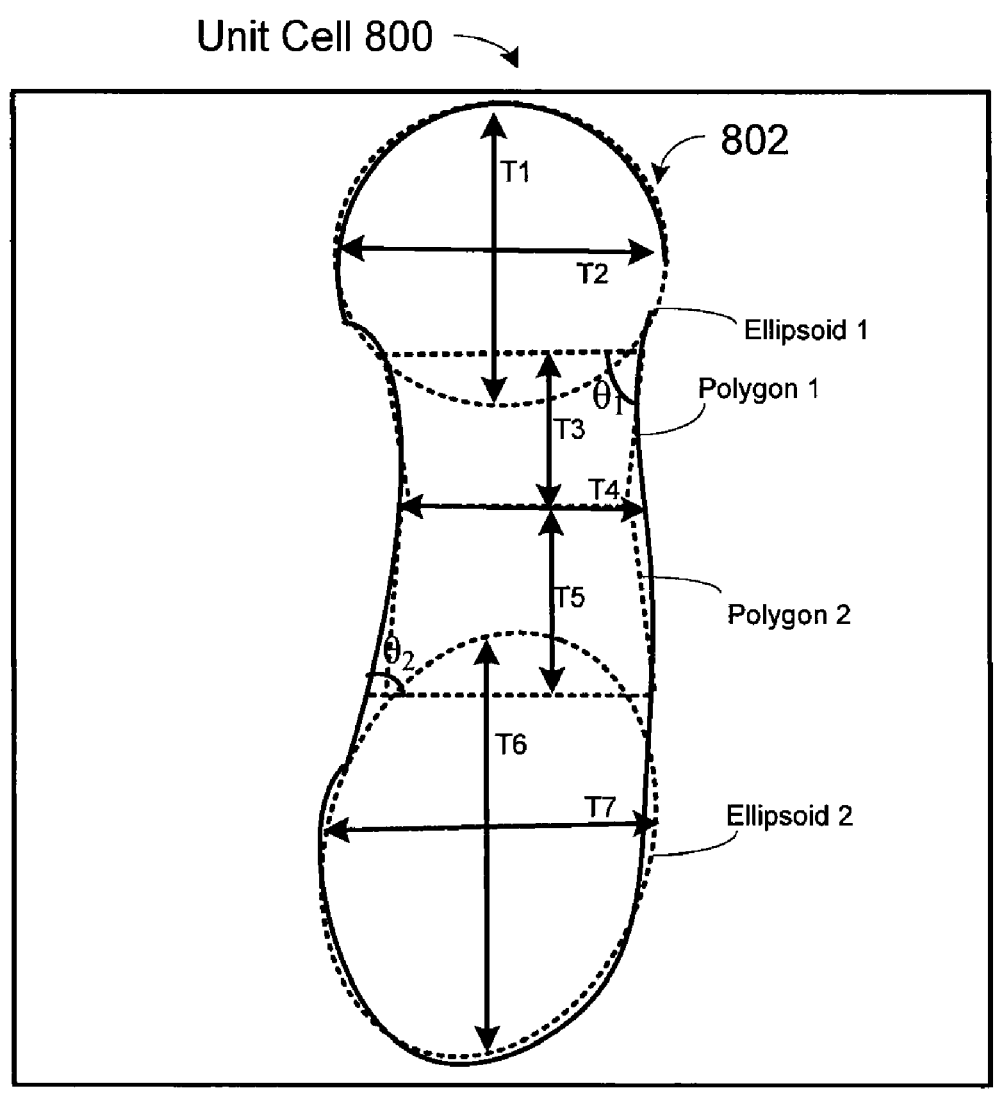
FIG. 13 is an exemplary technique for characterizing the top-view of a unit cell of a repeating structure.

An illustration of successive shape approximation technique shall be discussed in conjunction with FIG. 13. Assume that a SEM or AFM image of a unit cell 800 of a repeating structure is a feature 802, which is an island with a peanut shape viewed from the top. One approach would be to approximate the feature 802 with a variable number or combinations of ellipses and polygons.

Assume further that after analyzing the variability of the top-view shape of the feature 802, it was determined that two ellipses (Ellipsoid 1 and Ellipsoid 2) and two polygons (Polygon 1 and Polygon 2) were found to fully characterize the feature 802. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; and T6 and T7 for Ellipsoid 2. Many other combinations of shapes could be used to characterize the top-view of the feature 802 in unit cell 800.

The mathematical approach utilizes a mathematical formula to describe a shape of the feature of the in the unit cell. Starting with the top-view of the unit cell, a formula is selected that can best express the shape of feature. If the top-view profile of the feature is close to an ellipse, a general ellipse formula may be used such as equation 1.10 or a Fourier synthesis of the general ellipse formula such as equation 1.20. Alternatively, a set of equations may be used that characterizes the variability of the collected profiles of the repeating structure, such as the set of equations in 2.10 and 2.20. Regardless of the shape, if one or more mathematical formulae or expressions adequately characterize the variability of the top-view profiles, these equations can be used to characterize the top-view of the features in a unit cell. With respect to FIG. 13, the characterization of feature 802 in unit cell 800 would typically include a set of equations representing the two ellipses (Ellipsoid 1 and Ellipsoid 2) and the two polygons (Polygon 1 and Polygon 2).

Other embodiments may employ classic geometric shapes such as ellipses but altered by using automated drafting techniques to change the axis or center of rotation. For example, an ellipse may be configured to look more like a peanut-shaped profile using such techniques. Even arbitrary shapes made possible using automated techniques, use of software that utilize multiple axes of rotations and centers, could be used to characterize the view of the structure that is under investigation.

With reference to FIG. 12, in step 720, profile parameters are selected to represent variations in the top-view profile of the structure. Selection of parameters may be based on historical data and/or progressive inclusion of select parameters or successive exclusion of select parameters. Use of historical data such as previous experience with a similar recipe or fabrication process may be sufficient to get to the least number of top-view profile parameters to get good simulation results. For example, if a previous recipe for contact hole basically used a very similar recipe and good simulation results were obtained with a single ellipsoid model, then the final selection of top-view profile parameters for that application may be used as the starting selection for the current application. Progressive inclusion of new top-view profile parameters starts with one or more profile parameters that show significant variability based on profile data gathered.

For example, with reference to FIG. 13, assume that top-view profile parameters T2 (a dimension of Ellipsoid 1) and T7 (a dimension of Ellipsoid 2) showed the most variability while the rest of the top-view profile parameters were relatively constant. Then, T2 and T7 would be selected to represent the variations of the top-view profile in the optical metrology model in step 720, FIG. 12. Alternatively, if only T7 of Ellipsoid 2 showed the most variability, only T7 may be selected.

With reference to FIG. 12, in step 730, profile parameters associated with the cross-sectional view profile of the structure are selected. Cross-sectional view profile parameters include the polar angle of incidence of the incident beam, the azimuthal angle of incidence of the incident beam, the polarization angle of the incident, X-pitch, Y-pitch, pitch angle, width of the various layers, N and K of the various layers or N and K of the various features of the repeating structure within the unit cell, height of the feature, width of the feature at various points, sidewall angle, footing or top rounding of the feature, and the like. Similar to the process used in selecting the top-view profile parameters, selection of parameters may be based on historical data and/or successively making select parameters fixed instead of variable. Use of historical data such as previous experience with a similar recipe or fabrication process may be sufficient to get to the least number of variable cross-sectional view profile parameters to get good simulation results.

In step 740 of FIG. 12, the selected top-view and cross-sectional view profile parameters are integrated into an optical metrology model. As described above, in integrating the selected profile parameters, redundancies are removed.

In step 750 of FIG. 12, the optical metrology model is optimized. Optimization of metrology models typically involved a regression-based process. The output of this step is an optimized metrology model based on the selected profile parameters and one or more termination criteria. Examples of termination criteria include goodness of fit, cost function, sum squared error (SSE), and the like. For a detailed description of regression-based processes, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

Referring to FIG. 12, in step 760, sets of profile parameters and corresponding diffraction signals are created using the optimized metrology model. A profile parameter set includes the profile parameters selected in step 720 and 730. The corresponding diffraction signal is created by simulating the diffraction off the repeating structure using a profile parameter set. For example, a library can be generated using the ranges of the selected profile parameters and appropriate resolutions for each profile parameter. A machine learning system (MLS) may be trained with a subset of the library created. A combination of regression and library generation techniques may be used to generate either a library or a trained MLS capable of creating new diffraction signals from an input set of profile parameters or extracting a set of profile parameters for an input measured diffraction signal.

In step 770, measured diffraction signals are matched against the simulated diffraction signals created using the sets of profile parameters derived from the optimized metrology model to determine the best match.

In step 780, using the measured and the best match simulated diffraction signal, the one or more matching criteria are calculated. Goodness of fit, cost function, SSE, and the like may be used as matching criteria. If the matching criteria are not met, then the characterization of the features in the unit cell and/or the selection of top-view profile parameters may be altered, as in step 790.

For example, assume one or more measured diffraction signals off a repeating structure with a unit cell similar to unit cell 800 depicted in FIG. 13. Further assume that top-view profile parameters T2 and T7 of feature 802 in FIG. 13 were selected. In step 780, the matching criteria values are calculated and compared to preset matching criteria. Assume the preset matching criteria include goodness of fit of not less than 95% and a cost function of no more than 2.50. If the calculated matching criteria show a goodness of fit of 96% and a cost function of 2.40, then the matching criteria are met and processing proceeds to step 800.

Otherwise, in step 790, characterization of the top-view profile of the structure and/or selection of top-view profile parameters of the repeating structure are revised. Revision of characterization of the top-view profile may include using three instead of two polygons to characterize the middle portion of feature 802 in FIG. 13. As discussed above, revision of the selection of profile parameters depends on the technique used. If progressive inclusion of new parameters is used, one or more top-view profile parameters may be added to the group of selected top-view profile parameters. Referring to FIG. 13, if only T2 and T7 were the two previously selected top-view profile parameters, revision of the selection may result in adding T 4 and/or T6 if T4 and/or T6 showed some significant variability in the collected profile data.

If successive exclusion of profile parameters is used, then the matching criteria are set up accordingly. For example, the preset matching criteria may include goodness of fit of not more than 94% and a cost function of not less than 2.30. If the calculated matching criteria show a goodness of fit of 96% and a cost function of 1.90, then the matching criteria are not met and processing proceeds to step 790. In step 790, characterization of the top-view profile of the structure and/or selection of top-view profile parameters of the repeating structure are revised. Revision of characterization of the top-view profile may include using three instead of two polygons to characterize the middle portion of feature 802 in FIG. 13. With reference to the successive exclusion of profile parameters technique, the one or more top-view profile parameters are excluded to the group of selected top-view profile parameters. Referring to FIG. 13, if T1 to T7 were all previously selected top-view profile parameters, revision of the selection may result in excluding T3 and/or T5 if T3 and/or T5 showed less variability than the other top-view profile parameters in the collected profile data.

The cross-sectional view profile parameters of the repeating structure are processed in a similar manner, changing the type of shapes used to approximate the cross-sectional view profile and progressively fixing more parameters until the matching criteria are met. For a more detailed discussion of cross-sectional view profile shape and profile parameter selection, refer to U.S. patent application Ser. No. 10/206, 491, titled MODEL AND PARAMETER SELECTION FOR OPTICAL METROLOGY, filed on Jul. 25, 2002, which is incorporated herein by reference in its entirety.

In either technique, once the matching criteria are met, in step 800 of FIG. 12, profile parameters corresponding to the best match diffraction signal are extracted and transformed to the actual profile parameters. For example, referring to FIG. 13, the extracted top-view profile parameters may only include T2 and T7 of feature 802. This step transform values of T2 and T7 to the set of values of all the top-view profile parameters T1 to T7, $\theta_1$, and $\theta_2$ by utilizing correlation factors associated with the T2 and T7 to the rest of the top-view profile parameters.

Figure 14:
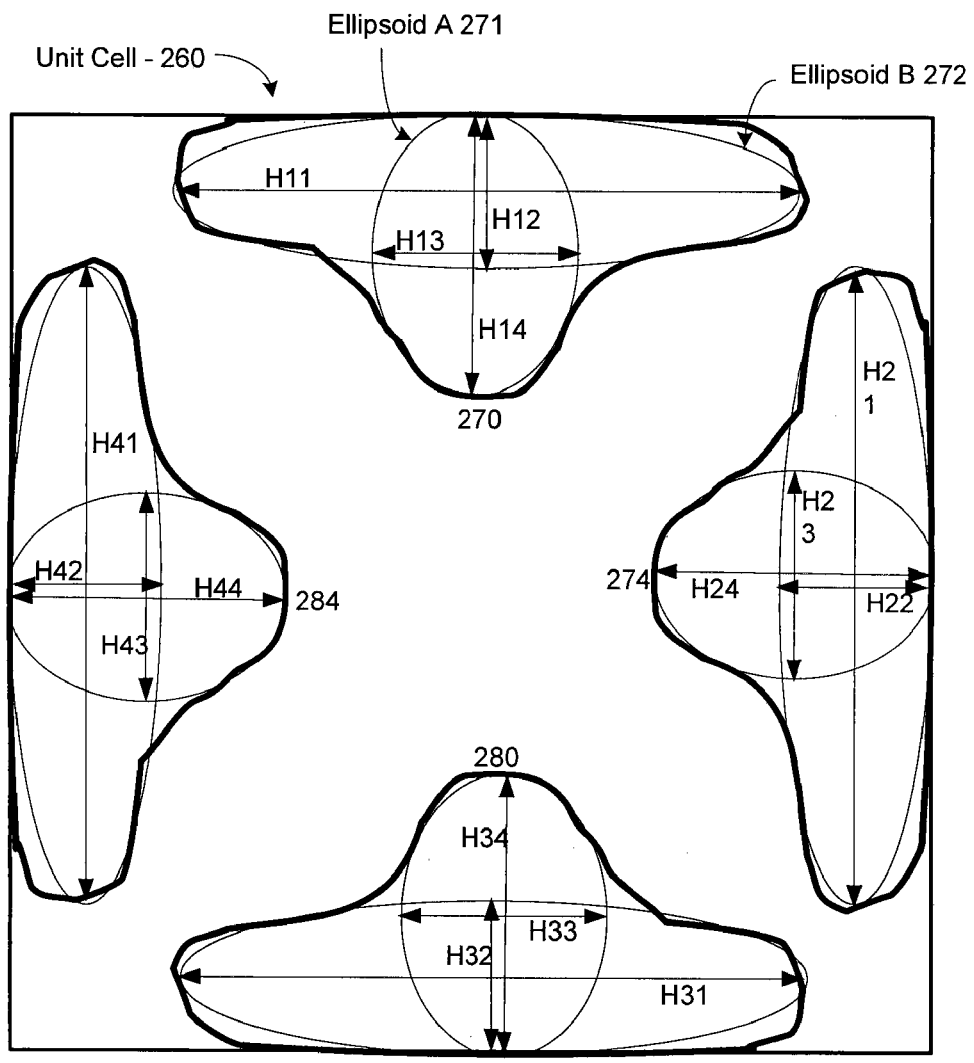
FIG. 14 is an exemplary technique for characterizing the top-view of a repeating structure with multiple features.

The same concepts and principles apply to a repeating structure where the unit cell has more than one structure feature as in FIG. 14. The unit cell 260 has features 270, 274, 280, and 284. With reference to feature 270, assume that profile data collected for the application indicate that the top-view profile of feature 270 may be approximated using two ellipses, Ellipsoid A 271, and Ellipsoid B 272. The major axis and minor axis of Ellipsoid A 271 are designated H11 and H12, respectively; the major axis and minor axis of Ellipsoid B 272 are designated H13 and H14, respectively. The other features, 274, 282, and 284 have major and minor axes of its respective ellipsoids designated as H21, H22, H23, and H24; H31, H32, H33, and H34; and H41, H42, H43, and H44, respectively.

As discussed above, when the progressive inclusion technique is used, depending on the variability of top-view profile data collected, only the major axes of the larger of two ellipsoids may be selected to model features in unit cell 260. Specifically, parameters H14, H24, H34, and H44 may be specified as the selected top-view profile parameters for optimization. If the matching criteria are not met, then successive iterations of the optimization may include the other top-view profile parameters of the features of the unit cell 260.

When the successive exclusion technique is used, initially, all the axes of all the ellipsoids may be used to model the features in unit cell 260. Specifically, parameters H11 to H14, H21 to H24, H31 to H34, and H41 to H44 may be specified as the selected top-view profile parameters for optimization. If the matching criteria are not met, then successive iterations of the optimization may exclude the other top-view profile parameters of the features of the unit cell 260.

As discussed above, a unit cell may include a combination of holes, trenches, vias or other concave shapes. A unit cell may also include a combination of posts, islands or other convex shapes or a combination of convex-type or concave-type shapes.

Figure 15:
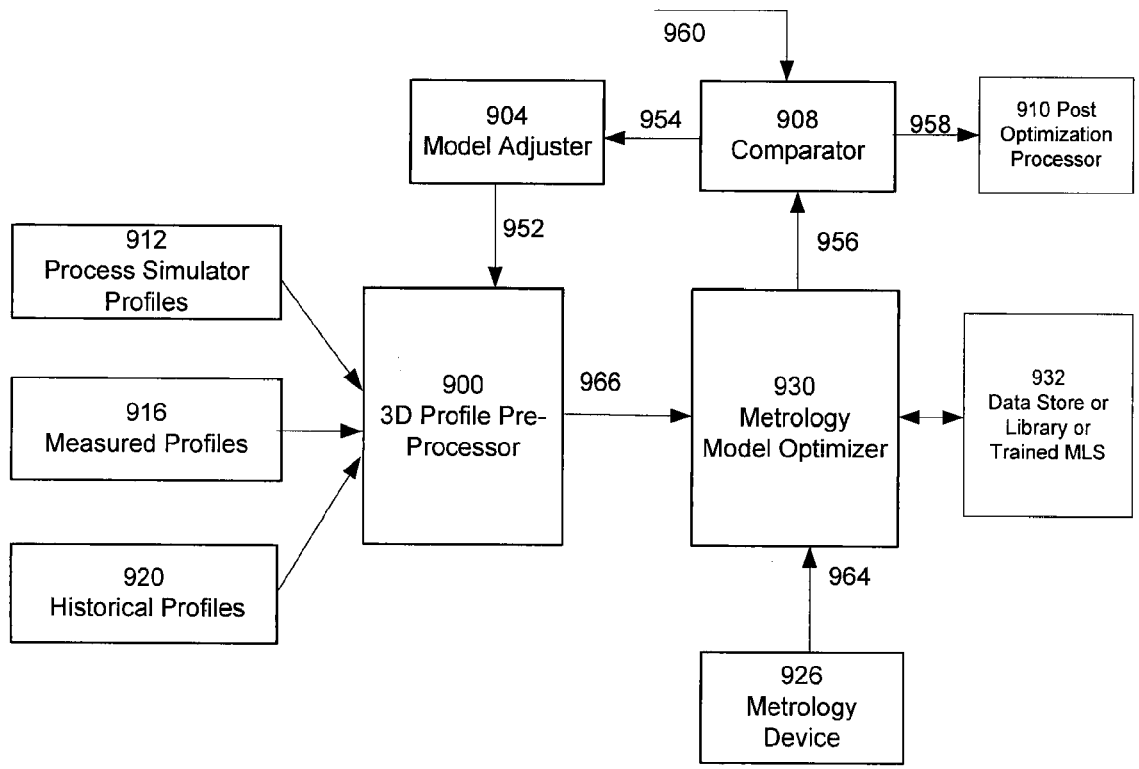
FIG. 15 is an exemplary system for optimizing an optical metrology model of a repeating structure.

FIG. 15 is an exemplary system for optimizing an optical metrology model of a repeating structure. A profile pre-processor 900 analyzes input process simulator top-view profiles 912, measured top-view profiles 916, and/or historical top-view profiles 920 of a repeating structure, (not shown). The profile pre-processor 900 selects specific top-view profile parameters and cross-sectional view profile parameters 966 of the structure and communicates the selected top-view profile parameters and cross-sectional view profile parameters 966 to the metrology model optimizer 930. The metrology model optimizer 930 processes the input measured diffraction signals 964 from the metrology device 926 and the selected profile parameters 966 to optimize the metrology model and extract the best match simulated diffraction signal 956 communicated to a comparator 908. The metrology model optimizer 930 may optionally use a library or data store comprising pairs of diffraction signals and profile parameters, or a machine learning systems trained to determine simulated diffraction signals from profile parameters or profile parameters from simulated diffraction signals. The comparator 908 calculates the values of the matching criteria and compares the calculated values with previously set matching criteria 960 and if the calculated values are not within the matching criteria, the comparator 908 communicates a signal 954 to the model adjuster 904 to determine an adjustment 952 to the optical metrology model. The model adjuster 904 communicates the adjustment or revisions 952 to the profile preprocessor 900 and iterates the cycle. If the calculated values are within the matching criteria, the comparator 908 terminates the optimization process and communicates the extracted profile parameter values 958 to the post optimization processor 910.

Although exemplary embodiments have been described, various modifications can be made without departing from the spirit and/or scope of the present invention. For example, a first iteration may be run with a high number of profile parameters and other metrology variables allowed to float. After the first iteration, variables that do not produce significant changes to the diffraction response may be set to fixed values. Alternatively, variables initially considered constant due to previous empirical data may be allowed to float after further analyses. For example, the X-offset and Y-offset or the pitch angle may be initially held constant but may be allowed to float in successive iterations due to additional profile data obtained. Furthermore, instead of ellipses and polygons, other shapes may utilized or the roughness of the shapes may be taken into account to provide a better or faster termination of the optimization process. Therefore, the present invention should not be construed as being limited to the specific forms shown in the drawings and described above but based on the claims below.

We claim:

1. A method of developing an optical metrology model for a structure to be formed on a wafer, wherein the optical metrology model is used in optical metrology to determine the profile of the structure after the structure is formed on the wafer, the method comprising:

characterizing a top-view profile of the structure using profile parameters;

characterizing a cross-sectional view profile of the structure using profile parameters;

integrating the profile parameters characterizing the top-view profile and the cross-sectional view profile of the structure into an optical metrology model; and storing the profile parameters of the optical metrology model.

2. The method of claim 1, wherein characterizing the top-view profile of the structure comprises:

defining a unit cell of the structures, the unit cell having one or more features; and characterizing the top-view profile of the one or more features of the unit cell using profile parameters.

3. The method of claim 2, wherein characterizing the top-view profile of the one or more features of the unit cell comprises:
fitting one or more basic shapes to the top-view profile of the one or more features of the unit cell;
identifying parameters of the one or more basic shapes; and
determining variability of the identified parameters of the one or more basic shapes.

4. The method of claim 3, wherein the basic shapes comprises ellipses and/or polygons.

5. The method of claim 4, wherein the identified parameters of the one or more basic shapes include ellipse minor axis, ellipse major axis, or length of one or more sides of a polygon.

6. The method of claim 3, further comprising:
selecting one or more identified parameters of the one or more basic shapes fitted to the top-view profile of the one or more features of the unit cell with the largest ranges of values, wherein the selected parameters correspond to the profile parameters.

7. The method of claim 2, wherein the one or more unit cells are defined by a hypothetical grid of lines.

8. The method of claim 2, wherein the profile parameters that characterize the top-view profile includes width ratio and rectangularity of the features in the unit cell.

9. The method of claim 2, wherein characterizing the top-view profile of the one or more features of the unit cell comprises:
fitting one or more mathematical models to the top-view profile shapes of the one or more features of the unit cell;
identifying parameters of the one or more mathematical models; and
determining the variability of the identified parameters of the one or more mathematical models.

10. The method of claim 9, wherein the mathematical models comprises equations for geometric shapes.

11. The method of claim 1, wherein integrating the profile parameters comprises:
removing any redundant profile parameters.

12. A method of determining the profile of a structure formed on a wafer, the method comprising:
a) characterizing a top-view profile of the structure using profile parameters;
b) characterizing a cross-sectional view profile of the structure using profile parameters;
c) integrating the profile parameters characterizing the top-view profile and the cross-sectional view profile of the structure into an optical metrology model;
d) obtaining a measured diffraction signal measured from the structure;
e) generating a simulated diffraction signal using a set of values for the profile parameters of the optical metrology model;
f) comparing the measured diffraction signal to the simulated diffraction signal; and
g) when the measured diffraction signal and the simulated diffraction signal do not match within a matching criterion, revising the set of values for the profile parameters and iterating steps e) to f).

13. The method of claim 12, further comprising:
when the measured diffraction signal and the simulated diffraction signal do match within the matching criterion, determining the profile of the structure to have values for the profile parameter of the optical metrology model used to generate the matching simulated diffraction signal.

14. The method of claim 12, wherein characterizing the top-view profile of the structure comprises:
defining a unit cell of the structures, the unit cell having one or more features; and
characterizing the top-view profile of the one or more features of the unit cell using profile parameters.

15. The method of claim 14, wherein characterizing the top-view profile of the one or more features of the unit cell comprises:
fitting one or more basic shapes to the top-view profile of the one or more features of the unit cell;
identifying parameters of the one or more basic shapes; and
determining variability of the identified parameters of the one or more basic shapes.

16. The method of claim 15, further comprising:
selecting one or more identified parameters of the one or more basic shapes fitted to the top-view profile of the one or more features of the unit cell with the largest ranges of values, wherein the selected parameters correspond to the profile parameters.

17. The method of claim 15, wherein characterizing the top-view profile of the one or more features of the unit cell comprises:
fitting one or more mathematical models to the top-view profile shapes of the one or more features of the unit cell;
identifying parameters of the one or more mathematical models; and
determining the variability of the identified parameters of the one or more mathematical models.

18. A system for developing an optical metrology model for a structure to be formed on a wafer, wherein the optical metrology model is used in optical metrology to determine the profile of the structure after the structure is formed on the wafer, the system comprising:
a model preprocessor configured to: characterize a top-view profile of the structure using profile parameters; characterize a cross-sectional view profile of the structure using profile parameters; and integrate the profile parameters characterizing the top-view profile and the cross-sectional view profile of the structure into an optical metrology model; and
a data store configured to store the profile parameters of the optical metrology model.

19. The system of claim 18, a model adjuster configured to alter the characterization of the top-view profile or the cross-sectional view profile of the structure.

20. A computer-readable storage medium containing computer executable instructions for developing an optical metrology model for a structure to be formed on a wafer, wherein the optical metrology model is used in optical metrology to determine the profile of the structure after the structure is formed on the wafer, comprising instructions for:
characterizing a top-view profile of the structure using profile parameters;
characterizing a cross-sectional view profile of the structure using profile parameters;
integrating the profile parameters characterizing the top-view profile and the cross-sectional view profile of the structure into an optical metrology model; and
storing the profile parameters of the optical metrology model.

* * * * *